United States Patent [19]

Hale et al.

[11] Patent Number: 4,714,530

[45] Date of Patent: Dec. 22, 1987

[54] METHOD FOR PRODUCING HIGH PURITY QUATERNARY AMMONIUM HYDROXIDES

[75] Inventors: Cecil H. Hale; Alan R. Tanner; Bryan M. Hale, all of Austin, Tex.

[73] Assignee: Southwestern Analytical Chemicals, Inc., Austin, Tex.

[21] Appl. No.: 884,505

[22] Filed: Jul. 11, 1986

[51] Int. Cl.$^4$ .............................................. C25F 5/00
[52] U.S. Cl. .................................................. 204/131
[58] Field of Search ..................... 204/130, 73 R, 131

[56] References Cited

U.S. PATENT DOCUMENTS

| 4,394,226 | 7/1983 | Wade et al. | 204/72 |
| 4,425,202 | 1/1984 | Sullivan | 204/72 |
| 4,521,285 | 6/1985 | DeWitt et al. | 204/72 |
| 4,572,769 | 2/1986 | Shimizu | 204/59 |
| 4,578,161 | 3/1986 | Buonomo et al. | 204/102 |

FOREIGN PATENT DOCUMENTS 57-155390 of 1982 Japan .
60-100690 of 1985 Japan .
60-131985 of 1985 Japan .
60-131986 of 1985 Japan .

Primary Examiner—R. L. Andrews
Attorney, Agent, or Firm—Renner, Otto, Boisselle & Lyon

[57] ABSTRACT

A process is described for improving the purity of quaternary ammonium hydroxides. In one embodiment, the process of the present invention comprises the steps of
(a) charging an aqueous solution containing the quaternary ammonium hydroxide to the anolyte compartment of an electrolysis cell which comprises an anolyte compartment and a catholyte compartment containing water separated from each other by a cation-exchange membrane,
(b) passing a direct current through the electrolysis cell to produce a high purity quaternary ammonium hydroxide in the catholyte compartment, and
(c) recovering the high purity quaternary ammonium hydroxide from the catholyte compartment.

In a preferred embodiment, the aqueous solution containing the quaternary ammonium hydroxide charged to the anolyte compartment is heated to an elevated temperature for a given period of time prior to subjecting the quaternary ammonium hydroxide to the electrolytic process of the present invention.

The process of the present invention results in the formation of quaternary ammonium hydroxide solutions containing significantly reduced amounts of halogen (both ionic and latent), carbonates and/or metals, and the solutions also are characterized by improved color.

25 Claims, No Drawings

METHOD FOR PRODUCING HIGH PURITY QUATERNARY AMMONIUM HYDROXIDES

TECHNICAL FIELD

This invention relates to a method of improving the purity of quaternary ammonium hydroxides. The invention also relates to the improved high purity quaternary ammonium hydroxides obtained by the above method.

BACKGROUND OF THE INVENTION

Quaternary ammonium hydroxide such as tetramethyl ammonium hydroxide (TMAH) and tetraethyl ammonium hydroxide (TEAH) are strong organic bases that have been known for many years. Such quaternary ammonium hydroxides have found a variety of uses including use as a titrant for acids in organic solvents and as a supporting electrolyte in polarography. Aqueous solutions of quaternary ammonium hydroxides, particularly TMAH solutions, have been used extensively as a developer for photoresists in printed circuit board and microelectronic chip fabrication. Use of quaternary ammonium hydroxides in the electronics area requires that there be no residue following the normal post-bake period. In electronic applications, it is desirable that the aqueous solutions of quaternary ammonium hydroxides should be essentially free from metal ions such as sodium and potassium, and halides such as chlorine, bromine, iodine, etc. Particularly in recent years, there has been an increasing demand for quaternary ammonium hydroxides having a high purity.

Quaternary ammonium hydroxides such as TMAH and TEAH have been produced by various techniques. Generally, the quaternary ammonium hydroxides are manufactured by electrolyzing a salt of a quaternary ammonium in an electrolysis cell containing a diaphragm formed of a cation-exchange membrane. The quaternary ammonium salts used in such preparations include halogenated salts, carboxylate salts, carbonate salts and sulfate salts. When halogenated salts are used in the manufacture of quaternary ammonium hydroxide, it has been discovered that the quaternary ammonium hydroxide solutions formed by this method contain significant amounts of halogen (ionic and latent), generally in concentrations above 50 ppm and more generally above 100 ppm. The term "latent halide" is used throughout this specification and claims to refer to non-ionic halide which is present in the aqueous quaternary ammonium hydroxide solutions, and which is capable of forming halide ions under certain conditions such as, e.g., heating. The precise nature or form of the latent halide is not known at this time.

Among the prior art patents which describe the preparation of quaternary ammonium hydroxides by electrolyzing a salt of a quaternary ammonium compound are U.S. Pat. Nos. 4,572,769 and 4,394,226. U.S. Pat. No. 4,572,769 describes the use of formate salts to form the quaternary ammonium hydroxides, and this patent suggests that some of the problems of using quaternary ammonium halides are minimized by use of the formate salt. U.S. Pat. No. 4,394,226 describes production of quaternary ammonium hydroxides in electrolytic cells using cationic membranes which have been treated with a mineral acid prior to use in the electrolysis.

SUMMARY OF THE DISCLOSURE

A process is described for improving the purity of quaternary ammonium hydroxides. In one embodiment, the process of the present invention comprises the steps of (a) charging an aqueous solution containing the quaternary ammonium hydroxide to the anolyte compartment of an electrolysis cell which comprises an anolyte compartment and a catholyte compartment containing water separated from each other by a cation-exchange membrane, (b) passing a direct current through the electrolysis cell to produce a high purity quaternary ammonium hydroxide in the catholyte compartment, and (c) recovering the high purity quaternary ammonium hydroxide from the catholyte compartment.

In a preferred embodiment, the aqueous solution containing the quaternary ammonium hydroxide charged to the anolyte compartment is heated to an elevated temperature for a given period of time prior to subjecting the quaternary ammonium hydroxide to the electrolytic process of the present invention.

The process of the present invention results in the formation of quaternary ammonium hydroxide solutions containing significantly reduced amounts of halogen (both ionic and latent), carbonates and/or metals, and the solutions also are characterized by improved color.

DESCRIPTION OF THE PREFERRED EMBODIMENTS

The quaternary ammonium hydroxide solutions which are treated in accordance with the process of the present invention to improve the purity thereof generally are aqueous solutions containing quaternary ammonium hydroxides characterized by the formula

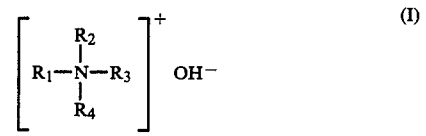

wherein $R_1$, $R_2$, $R_3$ and $R_4$ are each independently alkyl or hydroxyalkyl groups containing from one to about 10 carbon atoms, alkoxyalkyl groups containing from two to about 10 carbon atoms, aryl groups, or hydroxyaryl groups.

Specific examples of alkyl groups containing from one to 10 carbon atoms include methyl, ethyl, propyl, butyl, pentyl, hexyl, heptyl, octyl, nonyl, and decyl groups. $R_1$, $R_2$, $R_3$ and $R_4$ also may be hydroxyalkyl groups such as hydroxymethyl, hydroxyethyl and the various isomers of hydroxypropyl, hydroxybutyl, hydroxypentyl, etc. Specific examples of alkoxyalkyl groups include methoxymethyl, ethoxymethyl, ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

Examples of quaternary ammonium hydroxides which can be treated in accordance with the process of the present invention include tetramethylammonium hydroxide, tetraethylammonium hydroxide, tetrapropylammonium hydroxide, trimethylhydroxyethylammonium hydroxide, trimethylmethoxyammonium hydroxide, dimethyldihydroxymethylammonium hydroxide, methyltrihydroxyethylammonium hydroxide, phenyltrimethylammonium hydroxide, phenyltriethylammonium hydroxide, benzyltrimethylammonium hydroxide, etc.

In one preferred embodiment, the R groups are alkyl and hydroxyalkyl groups containing from one to 10 carbon atoms and more preferably one to three carbon atoms. Most often, the quaternary ammonium hydroxides treated in accordance with the process of the present invention will be tetramethylammonium hydroxide (TMAH) or tetraethylammonium hydroxide (TEAH).

The aqueous solutions of quaternary ammonium hydroxides which can be treated in accordance with the process of the present invention may be prepared by any of the known techniques. Generally, the quaternary ammonium hydroxides which are purified in accordance with the process of the present invention are quaternary ammonium hydroxides manufactured by electrolyzing quaternary ammonium salts, particularly a quaternary ammonium halide, in an electrolysis cell containing a diaphragm formed of a cation-exchange membrane. Procedures such as described in U.S. Pat. No. 4,394,226 and in other publications for the electrolysis of quaternary ammonium halides generally constitute the source of the quaternary ammonium hydroxides purified in accordance with the process of the present invention.

The quaternary ammonium hydroxides which are purified in accordance with the process of the present invention are aqueous solutions containing from about 3 to about 55% by weight or about 3 to about 50% by weight of the hydroxide and generally will contain significant amounts of halogen. For example, aqueous solutions of quaternary ammonium hydroxides prepared by the electrolysis of quaternary ammonium halides typically may contain at 25%w of quaternary ammonium hydroxide of from about 15 to about 200 ppm of ionic halide and from about 5 to about 75 ppm of latent halide. Unless otherwise specifically indicated in this application all references to, and analytical results relating to ppm of halide, metals, or carbonates are for aqueous solutions containing 25%w of the quaternary ammonium hydroxide.

In one embodiment, the purity of such quaternary ammonium hydroxides is improved in accordance with the process of the present invention by subjecting the quaternary ammonium hydroxides to the process which comprises the steps of (a) charging an aqueous solution containing the quaternary ammonium hydroxide to the anolyte compartment of an electrolysis cell which comprises an anolyte compartment and a catholyte compartment containing water separated from each other by a cation-exchange membrane, (b) passing a direct current through the electrolysis cell to produce a high purity quaternary ammonium hydroxide in the catholyte compartment, and (c) recovering the high purity quaternary ammonium hydroxide from the catholyte compartment.

As noted, the electrolysis cell utilized in the process of the present invention contains a cation-exchange membrane. The cation-exchange membrane may be any which have been used in the electrolysis of quaternary ammonium salts to quaternary ammonium hydroxides. Preferably, the cation-exchange membranes should comprise a highly durable material such as the membranes based on the fluorocarbon series, or from less expensive materials of the polystyrene or polypropylene series. Preferably, however, the cationic membranes useful in the present invention include fluorinated membranes containing cation exchange groups such as perfluorosulfonic acid and perfluorosulfonic acid/perfluorocarboxylic acid perfluorocarbon polymer membranes such as sold by the E. I. duPont de Nemours & Company under the trade designation "Nafion". Other suitable cation-exchange membranes include styrene-divinylbenzene copolymer membranes containing cation-exchange groups such as sulfonate groups, carboxylate groups, etc.

The type of electrolysis cell used in the process of the present invention may be any of the known electrolysis cells, and the cells may be composed of conventional cell materials which are compatible with the materials being charged into the cells. Since the anode and cathode do not directly enter into the reaction, they also may be made from a variety of materials that do not react with the solutions added to the cells. While a variety of such materials may be used, the anodes generally may be high purity graphite electrodes or a titanium electrode coated with an oxide of a material belonging to the platinum group. Other suitable anode materials include nickel and ruthenized titanium anodes. Cathode materials may include nickel plated titanium, solid nickel,, iron and stainless steel.

The concentraton of the quaternary ammonium hydroxide in the aqueous solutions charged into the anolyte compartment in accordance with the process of the present invention generally will be from about 3 to about 55% by weight or from about 3% to about 50% by weight. More generally the concentration will be from about 5 to about 30% by weight. During the electrolysis, it is desirable that the temperature of the liquid within the cells be maintained within the range of about 10° to about 70° C., and more generally, the temperature is maintained at 50° C. or below during electrolysis.

The water is charged into the catholyte compartment either before or after the aqueous quaternary ammonium hydroxide solution is charged to the anolyte compartment, but the water is charged before electrolysis is initiated. The water is preferably deionized water and more preferably, very pure deionized water. Demineralized water has low electric conductivity. When therefore, the demineralized water is supplied to the cathode chamber, difficulties arise in commencing electrolysis at the start of manufacturing the subject quaternary ammonium salt. It is therefore preferred to apply a demineralized water to which about 0.01 to 1.0% by weight of quaternary ammonium hydroxide is added.

The electrolysis of the aqueous solution containing the quaternary ammonium hydroxide is effected by impressing a direct current voltage between the anode and cathode with a current density of from about 5 to about 250 A/ft$^2$, and more preferably at a current density of from about 25 to about 150 A/ft$^2$. Alternatively the current density may be about 1–100 A/dm$^2$ or 10–50 A/dm$^2$. The current is applied to the cell for a period which is sufficient to result in the formation of the desired concentration of quaternary ammonium hydroxide in the catholyte compartment. Circulation is effected by pumping and/or by gas evolution. In practice, the electrolytic cell can be operated batchwise or in a continuous operation. Impure quaternary ammonium hydroxide can be added periodically or continuously to the anolyte compartment to maintain the appropriate concentration, and fresh water may be added periodically or continuously to the catholyte compartment as the purified quaternary ammonium hydroxide is removed from the catholyte compartment.

The application of the current through the cell results in the formation of an aqueous solution of the quaternary ammonium hydroxide in the catholyte compartment and this newly formed quaternary ammonium hydroxide is characterized by a much lower halide contamination than the original quaternary ammonium oxide solutions charged into the anolyte compartment at the beginning of the process.

The concentration of the quaternary ammonium hydroxide in the aqueous solution formed in the catholyte compartment will range from about 5 to about 40% by weight. The quaternary ammonium hydroxide formed in the catholyte compartment also is found to contain lesser amounts of other impurities contained in the original quaternary ammonium hydroxide solution such as alkaline earth metals, heavy metals, carbonates, etc. The typical product of this embodiment at 25%w of the quaternary ammonium hydroxide contains about 2–10 ppm of ionic chloride and about 16 to 30 ppm of latent chloride.

In the preferred embodiment, the aqueous solution containing the quaternary ammonium hydroxide which is charged into the anolyte compartment in step (a) is heated to an elevated temperature for an extended period of time prior to treatment in electrolysis cell. It has been discovered that the purity of the quaternary ammonium hydroxide recovered from the subsequent electrolysis step is improved when the original quaternary ammonium hydroxide is subjected to this preheating step. More specifically, the quaternary ammonium hydroxide solution which is to be charged to the anolyte compartment of the electrolysis cell is first heated to a temperature of from about 50° C. to about 200° C., and more preferably at a temperature of from about 80° C. to about 175° C. The heating generally is conducted for a period of from about 0.1 hour to about 4 days or more, and more generally for a period of from about 0.2 hour up to about 1 day. The length of time of the heating can be reduced by raising the temperature. However the temperature should not be so high as to result in the decomposition of significant amounts of the desired product. The heated quaternary ammonium hydroxide solution can be cooled prior to being charged to the anolyte compartment of the electrolysis cell, but cooling is not required. Although it is not understood completely why this preheating step improves the purity of the formed quaternary ammonium hydroxide recovered from the catholyte compartment, such pretreatment results in the recovery of quaternary ammonium hydroxides containing lesser amounts of halide impurities. It has been observed that this heating step per se does not reduce the ionic halide content of the heated material, and more often the heating step increases the ionic halide content. The latent halide content is, however, significantly reduced by the heating procedure. Typical properties of a 25% aqueous solution of quaternary hydroxide purified and recovered from the preferred process of this invention (pre-heating step included) are: 0–5 ppm of ionic halide; 0 ppm of latent chloride; 0–200 ppm of carbonate; no detectable heavy metals; and a colorless solution.

The following examples illustrate the process of the present invention. Unless otherwise indicated in the following examples, and elsewhere in the specification and claims, all parts and percentages are by weight, and all temperatures are in degrees centigrade.

EXAMPLE 1

An aqueous tetramethylammonium hydroxide solution (prepared by the electrolysis of the corresponding chloride in an electrolysis cell equipped with a cation-exchange membrane) containing 14% by weight of the hydroxide (1.5M), is used as the anolyte in a cell equipped with an iron cathode, ruthenium oxide anode and a Nafion 901 membrane (duPont). At 25%w TMAH this aqueous solution contains 99 ppm of ionic chloride and 41 ppm of latent chloride. Deionized water containing a small amount (about 0.1%) of the quaternary hydroxide is used as the catholyte. Electrolysis at about 50° C. and a current density of about 83 A/ft$^2$ yielded a 1.45M TMAH solution containing 10 ppm of ionic chloride and 9 ppm latent chloride at 25% TMAH.

EXAMPLE 2

A tetramethylammonium hydroxide solution similar to that used as the starting quaternary hydroxide in Example 1 but at 2.92M is heated and maintained at a temperature of about 90° C. for three days. At the end of this heating period, the solution, at 25% TMAH, contains 140 ppm of ionic chloride and no measurable latent chloride. The latent chloride appears to be converted to ionic chloride.

The solution is charged to the anolyte compartment of an electrolytic cell as in Example 1. Electrolysis is conducted at a current density of about 83 A/ft$^2$ until a 1.27M solution is obtained in the catholyte. The tetramethylammonium hydroxide solution is recovered from the catholyte compartment, and analysis of the recovered tetramethylammonium hydroxide solution at 25% TMAH indicates an ionic chloride concentration of 3.9 ppm and no detectable latent chloride.

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

We claim:

1. A process of improving the purity of quaternary ammonium hydroxides obtained by the electrolysis of the corresponding quaternary ammonium salt which comprises the steps of
    (a) charging an aqueous solution containing the quaternary ammonium hydroxide to the anolyte compartment of an electrolysis cell which comprises an anolyte compartment and a catholyte compartment containing water separated from each other by a cation-exchange membrane,
    (b) passing a direct current through the electrolysis cell to produce a high purity quaternary ammonium hydroxide in the catholyte compartment, and
    (c) recovering the high purity quaternary ammonium hydroxide from the catholyte compartment.

2. The method of claim 1 wherein the quaternary ammonium hydroxide is characterized by the formula

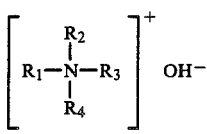

wherein $R_1$, $R_2$, $R_3$ and $R_4$ are each independently alkyl or hydroxyalkyl groups containing from one to about 10 carbon atoms, alkoxyalkyl groups containing from two to about 10 carbon atoms, aryl groups, or hydroxyaryl groups.

3. The method of claim 2 wherein $R_1$, $R_2$, $R_3$ and $R_4$ are each independently alkyl or hydroxyalkyl groups containing one to three carbon atoms.

4. The method of claim 2 wherein $R_1$, $R_2$, $R_3$ and $R_4$ are methyl or ethyl groups.

5. The method of claim 1 wherein the quaternary ammonium salt is a quaternary ammonium halide.

6. The method of claim 5 wherein the quaternary ammonium halide is a quaternary ammonium chloride.

7. The method of claim 1 wherein the cation-exchange membrane comprises a perfluorosulfonic acid or a perfluorosulfonic acid/perfluorocarboxylic acid perfluorohydrocarbon polymer membrane.

8. The process of claim 1 wherein the concentration of the quaternary ammonium hydroxide in the aqueous solution charged in step (a) is from about 3 to about 55% by weight.

9. The process of claim 8 wherein the concentration is from about 5 to about 30% by weight.

10. The method of claim 1 wherein the aqueous solution containing the quaternary ammonium hydroxide charged to the anolyte compartment is heated at an elevated temperature of from about 50° C. to about 200° C. for a period of from about 0.1 hour to about 4 days prior to being charged to the anolyte compartment in step (a).

11. A process for improving the purity of quaternary ammonium hydroxides prepared by electrolyzing a quaternary ammonium halide salt in an electrolysis cell containing a cation-exchange membrane which comprises the steps of
(a) charging an aqueous solution containing said quaternary ammonium hydroxide into the anolyte compartment of an electrolysis cell comprising an anolyte compartment and a water-containing catholyte compartment separated by a cation-exchange membrane, said aqueous solution containing a concentration of halide ions, and said quaternary ammonium hydroxide being characterized by the formula

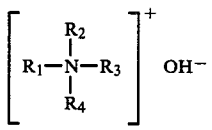

wherein $R_1$, $R_2$, $R_3$ and $R_4$ are each independently alkyl or hydroxyalkyl groups containing from one to about 10 carbon atoms,
(b) passing a direct current into the electrolysis cell for a period of time effective to form a quaternary ammonium hydroxide in the catholyte compartment, and
(c) recovering the quaternary ammonium hydroxide from the catholyte compartment, said quaternary ammonium hydroxide containing less halogen than the amount of halogen present in the quaternary ammonium hydroxide charged to the anolyte compartment in step (a).

12. The process of claim 11 wherein the concentration of quaternary ammonium hydroxide in the aqueous solution recovered in step (c) is between about 5 to about 40% by weight.

13. The process of claim 11 wherein $R_1$, $R_2$, $R_3$ and $R_4$ each contain one or two carbon atoms.

14. The process of claim 11 wherein $R_1$, $R_2$, $R_3$ and $R_4$ are methyl groups.

15. The process of claim 11 wherein the quaternary ammonium hydroxide solution charged in step (a) is heated at a temperature of from about 50° to about 200° C. for a period of at least about 0.1 hour prior to being charged to the anolyte compartment in step (a).

16. The process of claim 15 wherein the aqueous solution is heated at a temperature of from about 80° to about 175° C. for a period of about 0.1 hour to about 4 days.

17. A process for reducing the halide content of quaternary ammonium hydroxides prepared by the electrolysis of quaternary ammonium halides which comprises the steps of
(a) heating said quaternary ammonium hydroxide at an elevated temperature of from about 50° to about 200° C. for a period of at least about 0.1 hour,
(b) charging said aqueous quaternary ammonium hydroxide solution obtained in step (a) into the anolyte compartment of an electrolysis cell comprising an anolyte compartment and a water-containing catholyte compartment separated by a cation-exchange membrane,
(c) passing a direct current through the electrolysis cell for a period of time sufficient to form the quaternary ammonium hydroxide in the catholyte compartment, and
(d) recovering the quaternary ammonium hydroxide solution from the catholyte compartment, said solution containing less halide than the solution heated in step (a).

18. The process of claim 17 wherein the quaternary ammonium hydroxide is represented by the formula

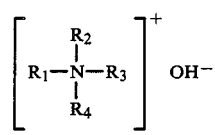

wherein $R_1$, $R_2$, $R_3$ and $R_4$ are each independently alkyl or hydroxyalkyl groups containing from one to about 10 carbon atoms.

19. The process of claim 18 wherein $R_1$, $R_2$, $R_3$ and $R_4$ contain from one to three carbon atoms.

20. The process of claim 18 wherein $R_1$, $R_2$, $R_3$ and $R_4$ are methyl groups.

21. The process of claim 17 wherein the cation-exchange membrane is a perfluorosulfonic acid or a perfluorosulfonic acid/perfluorocarboxylic acid perfluorocarbon polymer membrane.

22. The process of claim 17 wherein the quaternary hydroxide heated in step (a) is obtained by the electrolysis of the corresponding chloride.

23. The aqueous quaternary ammonium hydroxide obtained by the process of claim 1.

24. The aqueous quaternary ammonium hydroxide obtained by the process of claim 11.

25. The aqueous quaternary ammonium hydroxide obtained by the process of claim 17.

* * * * *